United States Patent [19]

Ikeda et al.

[11] Patent Number: 5,578,622

[45] Date of Patent: Nov. 26, 1996

[54] ISOTHIAZOLE DERIVATIVES AND THEIR USES

[75] Inventors: Kenichi Ikeda, Kawanishi; Katsutoshi Endo; Tsutomu Nishiguchi, both of Kawachinagano; Yoshimi Niwano, Osakasayama, all of Japan

[73] Assignee: Asamura Patent Office, Tokyo, Japan

[21] Appl. No.: 496,764

[22] Filed: Jun. 29, 1995

[30] Foreign Application Priority Data

Jun. 30, 1994 [JP] Japan .................................. 6-171806

[51] Int. Cl.⁶ .................... A01N 43/80; A61K 31/425; C07D 275/03
[52] U.S. Cl. .................... 514/372; 504/269; 504/225; 504/235; 514/236.8; 514/252; 548/213; 544/133; 544/367
[58] Field of Search .................... 548/213; 514/372; 504/269; 544/133, 367

[56] References Cited

U.S. PATENT DOCUMENTS

| | | | |
|---|---|---|---|
| 3,375,161 | 3/1968 | Volpp | 167/33 |
| 3,403,209 | 9/1968 | Bushong et al. | 424/270 |
| 3,481,946 | 12/1969 | Schmidt et al. | 260/302 |
| 3,720,769 | 3/1973 | Hoyer et al. | 424/270 |
| 4,053,479 | 10/1977 | Miller et al. | 260/302 A |
| 4,094,880 | 6/1978 | Goralski et al. | 260/302 SD |
| 4,143,043 | 3/1979 | Goralski et al. | 260/302 S |
| 4,170,704 | 10/1979 | Brandman et al. | 546/290 |

FOREIGN PATENT DOCUMENTS 1224663  3/1971  United Kingdom .

OTHER PUBLICATIONS

Chemical Abstracts, vol. 67, 100136a, 1967.
Chemical Abstracts, vol. 62, No. 9 (10373c) Apr. 1965 re: JP-A 39 019 791.
Chemical Abstracts, vol. 73, No. 9 (45497r) Aug. 1970 re: JP-A 45 014 300.
Chemical Abstracts, vol. 90, No. 25 (204080u) Jun. 1979 re: JP-A 54 022 365.
Chemical Abstracts, vol. 119, No. 8 (74715j) Aug. 1993 re: JP-A 04 325 568.
Budesinsky et al., "5–(3–IODOPROPARGYLOXY)Pyrimidines as Effective Fungistatics", Collection Czechoslov. Chem. Commun. (1975) 40:1078–1088.
Koyama et al., "Synthesis and Quantitative Structure—Activity Relationship Analysis of N–Triiodoallyl–and N–Iodopropargylazoles. New Antifungal Agents", Journal of Medicinal Chemistry (1987) 30:552–562.

Primary Examiner—Johann Richter
Assistant Examiner—Laura R. Cross
Attorney, Agent, or Firm—Cushman Darby & Cushman

[57] ABSTRACT

As isothiazole derivative represented by the formula (I),

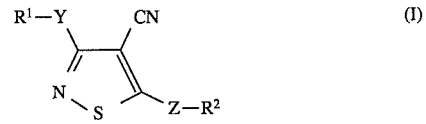

wherein $R^1$, $R^2$, Y and Z have the same meanings as defined in the description of the specification, and it is useful as an active ingredient for fungicidal and/or bactericidal compositions for use in industry, agriculture and medical treatment.

9 Claims, No Drawings

ISOTHIAZOLE DERIVATIVES AND THEIR USES

BACKGROUND OF THE INVENTION

1. Field of the Invention

The present invention relates to a novel isothiazole derivative and use of this compound as a fungicide and/or bactericide.

2. Related Art

A fairly large number of isothiazole derivatives having a fungicidal and/or bactericidal activity are known as reported, for example, in G.B. pat. No. 1224663A, U.S. Pat. No. 3481946, U.S. Pat. No. 3375161, Chemical Abstracts, 67, 100136 (1967), etc. However, the fungicidal and/or bactericidal activities of those known isothiazole derivatives also are not said to be satisfactory.

SUMMARY OF THE INVENTION

The present invention provides a novel isothiazole derivative and fungicides and/or bactericides containing this compound as an active ingredient.

With notice given to the fungicidal and/or bactericidal activity of isothiazole derivatives, the present inventors examined the fungicidal and/or bactericidal activity of the derivatives by introducing various kinds of substituent. As a result, the present inventors found that isothiazole derivatives substituted with an iodoalkynyloxy, iodoalkynyloxyalkyloxy or iodoalkynyloxyalkylthio group, these derivatives being unknown in the literature, have a strong fungicidal and/or bactericidal activity, and that these derivatives are useful as fungicides and/or bactericides in various fields. The present inventors thus completed the present invention.

The present compound has an excellent fungicidal and/or bactericidal action on various diseases of plants, wood-rotting fungi and diseases of man and animals, and is useful as fungicides and/or bactericides for use in agriculture, industry and medical treatment.

DETAILED DESCRIPTION OF THE INVENTION

The present invention relates to an isothiazole derivative represented by the formula (I),

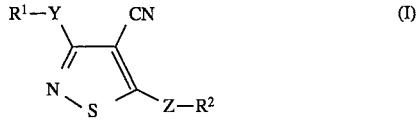

wherein $R^1$ represents a hydrogen atom, $C_1$–$C_6$ alkyl, $C_2$–$C_7$ alkenyl, $C_3$–$C_7$ alkynyl, $C_3$–$C_7$ cycloalkyl, $C_1$–$C_6$ cyanoalkyl, $C_1$–$C_6$ haloalkyl, $C_2$–$C_7$ alkoxyalkyl, $C_3$–$C_7$ alkoxycarbonylalkyl, $C_2$–$C_7$ haloalkenyl, $C_2$–$C_7$ alkylcarbonyl, $C_2$–$C_7$ alkoxycarbonyl, iodoalkynyl, or iodoalkynyloxyalkyl group, $R^2$ represents a $C_1$–$C_6$ alkyl, $C_2$–$C_7$ alkenyl, $C_3$–$C_7$ alkynyl, $C_3$–$C_7$ cycloalkyl, $C_1$–$C_6$ cyanoalkyl, $C_1$–$C_6$ haloalkyl, $C_2$–$C_7$ alkoxyalkyl, $C_3$–$C_7$ alkoxycarbonylalkyl, $C_2$–$C_7$ haloalkenyl, $C_2$–$C_7$ alkylcarbonyl, $C_2$–$C_7$ alkoxycarbonyl, iodoalkynyl, or iodoalkynyloxyalkyl group, provided that at least one of $R^1$ and $R^2$ represents an iodoalkynyl or iodoalkynyloxyalkyl group, Y represents O or S, and Z represents O, S, SO, $SO_2$ or $NR^3$ in which $R^3$ represents a hydrogen atom, $C_1$–$C_6$ alkyl, $C_2$–$C_7$ alkenyl, $C_3$–$C_7$ alkynyl or benzyl group, or $R^3$ and $R^2$, taken together, represent a $C_3$–$C_5$ alkylene group which may contain O or N, and agricultural, industrial and medical fungicides and/or bactericides containing said compound as an active ingredient.

"For use in agriculture" referred to herein means use for protection of agricultural and horticultural crops, various fruit trees and various industrial crops. "For use in industry" means use for protection of various industrial materials such as prevention of wood, etc. from decay. "For use in medical treatment" means use for protection of man and animals from various diseases and treatment of such diseases.

In the definition of $R^1$ and $R^2$ in the formula (I), a $C_1$–$C_6$ alkyl group includes straight or branched alkyl groups such as methyl, ethyl, isopropyl, n-propyl, n-butyl, isobutyl, sec-butyl, tert-butyl, n-pentyl, n-hexyl, etc.; a $C_2$–$C_7$ alkenyl group includes 1-propenyl, 2-propenyl, 1-methyl-2-propenyl, 1,1-dimethyl-2-propenyl, butenyl, pentenyl, hexenyl, etc.; a $C_3$–$C_7$ alkynyl group includes 2-propynyl, 1-methyl-2-propynyl, 1,1-dimethyl-2-propynyl, butynyl, pentynyl, hexynyl, etc.; a cycloalkyl group includes cyclopropyl, cyclopentyl, cyclohexyl, etc.; a cyanoalkyl group includes cyanomethyl, cyanoethyl, etc.; a $C_2$–$C_7$ alkoxyalkyl group includes methoxymethyl, methoxyethyl, ethoxymethyl, ethoxyethyl, etc.; a $C_1$–$C_6$ haloalkyl group includes chloroethyl, difluoromethyl, 1,1,1-trifluoromethyl, 1,1,1,2,2-pentafluoroethyl, etc.; a $C_3$–$C_7$ alkoxycarbonylalkyl group includes methoxycarbonylmethyl, ethoxycarbonylmethyl, n-propoxycarbonylmethyl, isopropoxycarbonylethyl, etc.; a haloalkenyl group includes 3-chloro-2-propenyl, 2-chloropropenyl, 4-chloro-2-butenyl, etc.; a $C_2$–$C_7$ alkoxycarbonyl group includes methoxycarbonyl, ethoxycarbonyl, n-propoxycarbonyl, isopropoxycarbonyl, etc.; a $C_2$–$C_7$ alkylcarbonyl group includes methylcarbonyl, ethylcarbonyl, n-propylcarbonyl, isopropylcarbonyl, etc.; an iodoalkynyl group includes 3-iodo-2-propynyl, 4-iodo-3-butynyl, etc.; and an iodoalkynyloxyalkyl group includes 3-iodo-2-propynyloxymethyl, 1-methyl-3-iodo-2-propynyloxymethyl, 1,1-dimethyl-3-iodo-2-propynyloxymethyl, 1-(3-iodo-2-propynyloxy)ethyl, etc. Examples of a $C_3$–$C_5$ alkylene group in which $R^3$ and $R^2$, taken together, may contain O or N include pyrrolidino, morpholino, N-methylpiperazino, 1,2,4-triazol-1-yl, etc. which are formed by $R^3$, $R^2$ and an N atom to which $R^3$ and $R^2$ have been bonded.

Preferable isothiazole derivatives are those whose $R^1$ is $C_1$–$C_4$ alkyl, $C_2$–$C_5$ alkenyl or $C_1$–$C_4$ haloalkyl group, $R^2$ is $C_1$–$C_4$ alkyl, $C_2$–$C_5$ alkenyl, $C_1$–$C_4$ haloalkyl or $C_1$–$C_4$ cyanoalkyl group, provided that at least one of $R^1$ and $R^2$ is an iodoalkynyl or iodoalkynyloxyalkyl group, Y is a O or S, and Z is O, S or $SO_2$.

Most preferable isothiazole derivatives are those whose $R^1$ is $C_1$–$C_2$ alkyl, allyl or difluoromethyl group, $R^2$ is $C_1$–$C_2$ alkyl, allyl, difluoromethyl or cyanomethyl group, provided that at least one of $R^1$ and $R^2$ is iodopropargyl or iodopropargyloxymethyl group, Y is a O, and Z is O or S.

The isothiazole derivative represented by the formula (I) is produced according to the reaction formulae described below.

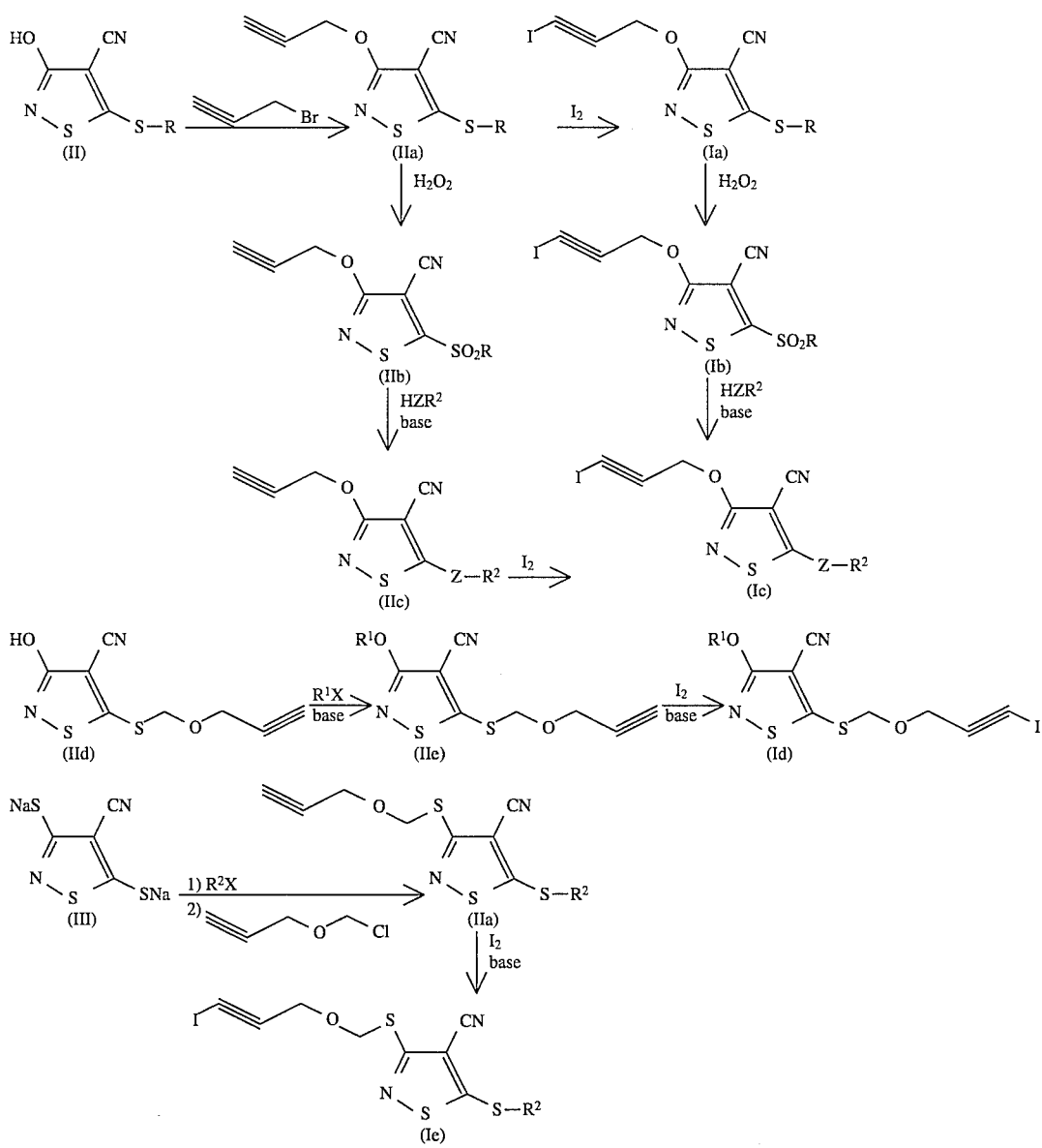

wherein $R^1$, $R^2$ and Z are as defined above, R represents an alkyl group and X represents a halogen atom.

A compound (II), a starting material, is alkynylated with an alkynyl halide at room temperature to 100° C. in the presence of a base (e.g. potassium carbonate, sodium methoxide) to obtain a compound (IIa). The compound (IIa) is then iodinated at 0° C. to 20° C. to synthesize a compound (Ia), which is then oxidized with a peracid (e.g. hydrogen peroxide) at room temperature to 100° C. to obtain a sulfoxide or sulfone (Ib). The sulfone (Ib) is substituted with an alcohol, thiol or amine at 0° C. to room temperature in the presence of a base to obtain a compound (Ic). This substitution may be carried out before iodination of the alkynyl group. That is, the compound (IIb) obtained by the oxidation of the compound (IIa) is substituted with an alcohol, thiol or amine to obtain a compound (IIc), and then the compound (Ic) can be synthesized by iodination of the compound (IIc). Similarly, compounds having an iodoalkynyloxyalkylthio group, etc. at the 5-position can also be synthesized. For example, a compound (IId), a starting material, is reacted in the presence of a base to obtain a compound (IIe), which is then iodinated to obtain a compound (Id). Also, a compound (III), a starting material, is successively and stepwise reacted with an alkyl halide and alkynyl halide to obtain a compound (IIIa), which is then iodinated to obtain a compound (Ie). The compounds (II) and (III), a material, can be synthesized by the methods described in the literatures [J.O.C., 28, 2163 (1962); J.O.C., 29, 665 (1965)], respectively.

In every reaction, any solvent may be used if it is a solvent which does not disturb the reaction. For example, there are given ketones such as acetone, methyl ethyl ketone, cyclohexanone, etc.; ethers such as diethyl ether, diisopropyl ether, dimethoxyethane, tetrahydrofuran, dioxane, monoglyme, diglyme, etc.; esters such as methyl acetate, ethyl acetate, etc.; halogenated hydrocarbons such as dichloroethane, chloroform, carbon tetrachloride, tetrachloroethane.; aromatic hydrocarbons such as benzene, chlorobenzene, nitrobenzene, toluene, etc.; nitriles such as acetonitrile, etc.; dimethylformamide (DMF), dimethyl sulfoxide, water and mixed solvents obtained by combination of these solvents. When a two-phase reaction is carried out with the mixed solvent, phase transfer catalysts such as triethylbenzylammonium chloride, trioctylmethylammonium chloride, etc. can also be used.

The present compound is useful as fungicides and/or bactericides for use in agriculture, industry and medical treatment. For example, in agriculture, it is excellent particularly as a seed disinfectant for paddy rice. In industry, it is used as a preservative and anti-molding agent for wood, water used in the manufacturing process of pulp, plastic articles and paints, an anti-molding agent for cosmetics and leather articles and an antimicrobial agent for clothing. In medical treatment, it is useful for disinfection of hands and feet of man and animals, and treatment and prevention of nosomycosis and candidiasis caused by fungi belonging to Candida and Trichophyton.

When the present compound is used as an agricultural and horticultural fungicide, it is very effective, for example, to control the following diseases: Blast of rice (*Pyricularia oryzae*), downy mildew of cucumber (*Pseudoperonospora cubensis*), phytophthora rot of tomato (*Phytophthora infestans*), late blight of other host plants, brown spot of grape (*Cladosporium cladosporioides*), seedling blight of rice (*Trichoderma viride*), alternaria leaf spot of apple (*Alternaria mali*), stem rot of sweet potato (*Fusarium oxysporum*), black mold of onion (*Aspergillus niger*), bacterial soft rot of onion (*Rhizopus nigricans*), "Bakanae disease" of rice (*Gibberella fujikuroi*), powdery mildew of barley and wheat (*Erysiphe graminis*), powdery mildew of cucumber (*Sphaerotheca fuliginea*), powdery mildew of apple (*Podosphaera leucotricha*), powdery mildew of grape (*Uncinula necator*), powdery mildew of other host plants, leaf rust of wheat (*Puccinia recondita*), crown rust of oat (*Puccinia coronata*) and rust of other host plants.

When the present compound is used as an industrial fungicide and/or bactericide, it is extremely effective, particularly, against wood-rotting fungi such as *Tyromyces palustris, Coriolus versicolor, Selupula lacrymas* and the like.

In order to formulate the present compound into agricultural and industrial fungicides and/or bactericides, the present compound is blended with a suitable inert carrier, if necessary together with auxiliaries, at a suitable proportion, and formulated into suitable preparation forms such as solution formulations, suspension formulations, oil sprays, emulsifiable concentrates, dusts, granules, wettable powders, tablets, pellets, paste formulations, aerosols and the like by operations such as dissolution, dispersion, suspension, mixing, impregnation, adsorption, adhesion and the like. The inert carrier usable in this formulation may be any of a solid, liquid and gas. Materials usable as the solid carrier include soybean powder, wood powder, bark powder, saw dust, tobacco stalk powder, walnut shell powder, bran, cellulose powder, residue after removing the extract of food, synthetic polymers (e.g. crushed synthetic resins), clays (e.g. kaolin, bentonite, acid clay), talcs (e.g. talc, pyrophyllite), silicas (e.g. diatomaceous earth, silica sand, mica, synthetic silicate, synthetic highly dispersible silicic acid), inorganic mineral powders such as activated carbon, sulfur powder, pumice, calcined diatomaceous earth, crushed brick, fly ash, sand, calcium carbonate, calcium phosphate, etc., chemical fertilizers such as ammonium sulfate, ammonium phosphate, ammonium nitrate, ammonium chloride, urea, etc., compost and the like. These carriers are used alone or in the form of a mixture of two or more of them.

Materials usable as the liquid carrier are selected from among those having a solvent capability by themselves and those which can disperse the active ingredient compound with the aid of auxiliaries if they have no solvent capability. For example, there are given the following ones, which are used alone or in the form of a mixture of two or more of them: Water, alcohols (e.g. methyl alcohol, isopropanol, ethylene glycol), ketones (e.g. acetone, cyclohexanone), ethers (e.g. ethyl ether, dioxane, tetrahydrofuran, cellosolve), aliphatic hydrocarbons (e.g. gasoline, kerosene), aromatic hydrocarbons (e.g. benzene, toluene, solvent naphtha, methylnaphthalene), halogenated hydrocarbons (e.g. dichloroethane, chloroform), esters (e.g. ethyl acetate, diisopropyl phthalate), amides (e.g. dimethylformamide, dimethylacetamide), nitriles (e.g. acetonitrile), dimethyl sulfoxide and the like.

The gaseous carrier includes freon gas, butane gas, dimethyl ether, carbon dioxide gas, LPG (liquefied petroleum gas) and the like.

The following compounds can be given as the auxiliaries. These auxiliaries are used according to the object, that is, they are used alone, in a mixture of two or more of them or, in some cases, they are not used at all. For the purpose of emulsification, dispersion, solubilization and/or wetting of the active ingredient compound, for example the following surface active agents can be used: Polyoxyethylene alkylaryl ether, polyoxyethylene alkyl ether, polyoxyethylene higher fatty acid ester, polyoxyethylene resin acid ester, polyoxyethylene sorbitan monooleate, alkylallylsorbitan monolaurate, alkylbenzenesulfonate, alkylnaphthalenesulfonate, lignin-sulfonate, the salt of a higher alcohol sulfuric acid ester, and the like.

For the purpose of dispersion. stabilization, pasting and/or bonding of the active ingredient compound, auxiliaries such as for example casein, gelatin, starch, alginic acid, CMC, gum arabic, agar, polyvinyl alcohol, turpentine, rice-bran oil, bentonite, lignin, sulfite waste liquid, and the like can also be used.

In order to improve the flowability of solid preparations, auxiliaries such as for example waxes, stearic acid, alkyl phosphate, etc. can be used.

As deflocculating agents for suspension preparations, there can also be used auxiliaries such as for example naphthalenesulfonic acid condensates, phosphates and the like.

Defoaming agents, for example silicone oil, etc., can also be added.

When the present compound is used as agricultural and horticultural fungicides, the proper amount of the active ingredient varies with various factors such as for example object of use, target crops, condition of growth of crops, tendency of outbreak of diseases, weather, environmental conditions, preparation forms, how, where and when the fungicides are used, and the like. However, the amount thereof is selected from the range of 0.1 g to 1 kg/10 ares.

The blending ratio of the active ingredient can be increased or decreased as need arises. When the active ingredient is formulated into dusts or granules, its blending ratio is usually 0.5 to 20%, and when it is formulated into emulsifiable concentrates, suspension formulations or wettable powders, its blending ratio is usually 0.1 to 90%.

The agricultural and horticultural fungicide containing the present compound as an active ingredient may also be used in mixture with other agricultural and horticultural fungicides with the object of decreasing the amount of the medicine in order to extend the range of target diseases to be controlled and to make longer a period during which the fungicides can be used for controlling. The agricultural and horticultural fungicides containing the present compound as an active ingredient shows a remarkable fungicidal effect on the foregoing diseases doing damage to crops in paddy field, crops in upland field, fruit trees, vegetables, other crops, flowers and ornamental plants, etc. Therefore, at a time when outbreak of the diseases is forecast, by just timely applying the fungicide to water in paddy field, soil in upland field and foliage of fruit trees, vegetables, other crops and flowers and ornamental plants before outbreak of the diseases or at a point when the outbreak has been confirmed, the agricultural and horticultural fungicide of the present invention exhibits an expected effect.

The industrial fungicide and/or bactericide containing the present compound as an active ingredient can be used in wood products such as plywood, products made of wood, particle boards, fiber boards and the like.

When the present compound is used for wood preservatives, it is applied to wood by means such as surface treatment, pressure injection and vacuum injection. The surface treatment is carried out by applying the present compound to wood part as it is or in dilution with water by coating, spraying, dipping and the like. Alternatively, by adding the present compound to a plywood adhesive and applying the adhesive, particularly, to building materials, the present compound can be used as a controlling agent for wood-rotting fungi.

The medicine used in the treatment varies with the kind of preparations, when, where and how the preparation is used, kind of wood-rotting fungi, degree of damage, etc. Usually, however, it will suffice to apply the medicine containing the active ingredient in an amount of 0.1 to 40 g per 1 $m^2$ of wood part.

When the present compound is used as wood preservatives, it may be used in mixture with other wood preservatives, insecticides, acaricides, termiticides, fungicides and/or bactericides or synergists with the object of decreasing the content of the active ingredient of the present invention or extending the effect of the active ingredient. The wood preservative used includes for example 3-iodo-2-propynyl-butylcarbamate, 3-iodopropargyl, zinc naphthenate, etc., and the termiticides used includes chlorpyrifos, phoxim, fenitrothion, permethrin, cypermethrin, fenvalerate and the like.

The present compound is also useful as antimycotic agents useful to disinfect the hands and feet of man and animals and treat mycotic infection. For example, these antimycotic agents can be used to treat local mycotic infection, mucosa infection and general mycotic infection caused by Trichophyton, Candida, Aspergillus and the like. The present compound is used alone, or, before use, it is mixed with a pharmaceutically acceptable inert carrier or diluent to prepare a composition, which is then formulated into preparations having a form suitable for oral or parenteral administration such as for example liquid formulations, tablets, suppositories, emulsions, ointments, creams, lotions, poultices and the like. If necessary, these preparations may contain auxiliaries, stabilizers, wetting agents or emulsifiers, buffer solutions and other commonly used additives. The amount of the compound administered varies with symptom, age, body weight, administration form, etc. In the case of general treatment, however, the amount is usually 0.05 to 100 mg, preferably 0.5 to 50 mg/1 kg of body weight/day/one adult, and this amount can be taken in one dose or several doses. In the case of local treatment, an optimum concentration of the active ingredient is 0.001% to 5%, preferably 0.1 to 2%.

WORKING EXAMPLE

Examples, prescription examples and test examples of the present invention will be shown, but the present invention is not to be interpreted as being limited to these examples alone.

Example 1

Synthesis of 3-(3-iodo-2-propynyloxy)-4-cyano-5-methylthioisothiazole (compound No. 1)

1.72 Grams of 3-hydroxy-4-cyano-5-methylthioisothiazole was dissolved in 20 ml of DMF, 0.7 g of potassium carbonate was added thereto, and then 1.3 g of propargyl bromide was added with stirring. After stirring at 50° C. for 1 hour, the reaction solution was ice-cooled, 3.0 g of iodine and 3.2 g of potassium iodide were added thereto, and then 6.6 g of a 10% KOH was gradually added dropwise with stirring. After addition, the reaction solution was stirred at room temperature for 1 hour. Water was added to the reaction solution to precipitate crystals, which were then collected by filtration and washed with water to obtain crude crystals. Recrystallization of the crude crystals from ether gave 2.5 g of crystals having a melting point of 145° to 146° C. (yield, 75%).

NMR (CDCl$_3$) δ: 2.67(3H, s), 5.14(2H, s).

Example 2

Synthesis of 3-(3-iodo-2-propynyloxy)-4-cyano-5-methylsulfonylisothiazole (compound No. 41)

3.36 Grams of 3-(3-iodo-2-propynyloxy)-4-cyano-5-methylthioisothiazole synthesized in Example 1 was dissolved in 50 ml of acetic acid, 5 g of aqueous hydrogen peroxide (30%) was added thereto, and then the reaction solution was heated at 80° C. for 5 hours with stirring. Water was added to precipitate crystals, which were then collected by filtration, washed with water and dried to obtain 2.8 g of white crystals having a melting point of 191° to 192° C. (yield 80%).

NMR (CDCl$_3$) δ: 3.37(3H, s), 5.23(2H, s).

Example 3

Synthesis of 3-(3-iodo-2-propynyloxy)-4-cyano-5-methoxyisothiazole (compound No. 21)

3.6 Grams of 3-(3-iodo-2-propynyloxy)-4-cyano5-methylsulfonylisothiazole synthesized in Example 2 was dissolved in 30 ml of methanol, 0.6 g of sodium methoxide was added thereto, and then the reaction solution was stirred at room temperature for 4 hours. Water was added to precipitate crystals, which were then collected by filtration, washed with water, dried and recrystallized from ether. Thus, 2.4 g of crystals having a melting point of 159° to 160° C. (yield 78%) was obtained.

NMR (CDCl$_3$) δ: 4.10(3H, s), 5.23(2H, s).

Example 4

Synthesis of 3-(3-iodo-2-propynyloxy)-4-cyano-5-dimethylaminoisothiazole (compound No. 30)

3.6 Grams of 3-(3-iodo-2-propynyloxy)-4-cyano-5-methylsulfonylisothiazole was dissolved in 30 ml of dimethoxyethane, 1.5 g of dimethylamine (as 50% aqueous solution) was added at room temperature with stirring, and then the reaction solution was stirred at 50° C. for 2 hours. Water was added to precipitate crystals, which were then collected by filtration, washed with water, dried and recrystallized from ethyl acetate. Thus, 2.2 g of white crystals having a melting point of 171° to 172° C. was obtained.

NMR (CDCl$_3$) δ: 3.22(3H, s), 5.08(2H, s).

Example 5

Synthesis of 3-(3-iodo-2-propynyloxymethyloxy)-4-cyano-5-ethylthioisothiazole (compound No. 86)

1.86 Grams of 3-hydroxy-4-cyano-5-ethylthioisothiazole was dissolved in 30 ml of DMF, and 0.7 g of potassium carbonate was added thereto. Thereafter, 1.3 g of 2-propynyloxymethyl chloride was added at room temperature with stirring, and the reaction solution was stirred at 50° C. for 2 hours. The reaction solution was ice-cooled to 5° to 10° C., a solution of 5.0 g of iodine and 3.2 g of potassium iodide in 5 ml of water and 20 ml of DMF was added thereto, and then 6.6 g of 10% KOH was added dropwise. After addition, the reaction solution was stirred at room temperature for 1 hour. Water was added to the reaction solution, which was then extracted with ethyl acetate. The extract was washed with water, dried and concentrated under reduced pressure to obtain crude crystals. Recrystallization of the crude crystals from ether/hexane gave 2.6 g of crystals having a melting point of 57° to 58° C.

NMR (CDCl$_3$) δ: 1.43–1.53(3H, t), 3.08–3.20(2H, q), 4.55(2H, s), 5.63(2H, s)

Example 6

Synthesis of 3-methoxy-4-cyano-5-(3-iodo-2-propynyloxymethylthio)isothiazole (compound No. 53)

2.18 Grams of 3-methyl-4-cyano-5-methylsulfonylisothiazole was dissolved in 20 ml of dimethoxyethane, and a solution of 1.2 g of potassium hydrosulfide (KSH) in 5 ml of water was added at room temperature with stirring. After stirring for 10 minutes, 1.3 g of 2-propynyloxymethyl chloride was added, and the reaction solution was stirred for 3 hours. Water was added to the reaction solution, which was then extracted with ethyl acetate. The extract was washed with water, dried and concentrated to obtain 2.1 g of an oily 3-methoxy-4-cyano-5-(2-propynyloxymethylthio)isothiazole. This product was dissolved in 20 ml of DMF and ice-cooled to 5° to 10° C. To this solution was added a solution of 5.1 g of iodine and 3.2 g of potassium iodide in 5 ml of water and 10 ml of DMF, and then 6.6 g of a 10% KOH was added dropwise. After addition, the reaction solution was stirred for 2 hours until the temperature reached room temperature. Water was added to the reaction solution, which was then extracted with ethyl acetate. The extract was washed with water, dried and concentrated under reduced pressure to obtain an oily product. This product was recrystallized from ether to obtain 2.7 g of white crystals having a melting point of 124° to 125° C. (yield 76%).

NMR (CDCl$_3$) δ: 4.03(3H, s), 4.52(2H, s), 5.20(2H, s).

Example 7

Synthesis of 3-(3-iodo-2-propynyloxymethylthio)-4-cyano-5-methylthioisothiazole (compound No. 128)

2.2 Grams of the disodium salt of 3,5-dimercapto-4-cyanoisothiazole was dissolved in 30 ml of DMF, and a solution of 1.5 g of methyl iodide in 20 ml of DMF was added dropwise while heating at 50° C. with stirring. After addition, the reaction solution was stirred for 20 minutes, and a solution of 1.2 g of 2propynyloxymethyl chloride in 20 ml of acetone was added dropwise thereto. After stirring for 1 hour, a solution of 5.1 g of iodine and 3.2 g of potassium iodide in 5 ml of water and 10 ml of DMF was added, and then 6.6 g of 10% KOH was added dropwise while ice-cooling and stirring. After addition, the temperature of the reaction solution was returned to room temperature, and after stirring for 2 hours, water was added to the reaction solution, which was then extracted with ethyl acetate. The extract was washed with water, dried and concentrated under reduced pressure to obtain crude crystals. The crystals were recrystallized from ether to obtain 3.2 g of crystals having a melting point of 87° to 88° C.

NMR (CDCl$_3$) δ: 2.64(3H, s), 4.54(2H, s), 5.70(2H, s).

Example 8

Synthesis of 3-methoxy-4-cyano-5-(4-iodo-3-butynyloxy)isothiazole (compound No. 80)

2.2 Grams of 3-methoxy-4-cyano-5-methylsulfonylisothiazole was dissolved in 20 ml of DMF, and 1.5 g of 3-butyn-1-ol and 4.3 g of 30% KOH were added at room temperature with stirring, after which the reaction solution was stirred for 2 hours. The reaction solution was ice-cooled to 5° to 10° C., 5.1 g of iodine and 3.2 g of potassium iodide were added thereto with stirring, and then 6.6 g of 10% KOH was added dropwise. The temperature of the reaction solution was returned to room temperature, and after stirring for 1 hour, water was added to the reaction solution, which was then extracted with ethyl acetate. The extract was washed with water, dried and concentrated under reduced pressure to obtain crude crystals. The crystals were recrystallized from ether to obtain 2.1 g of crystals having a melting point of 71° to 73° C.

NMR (CDCl$_3$) δ: 4.01(3H, s), 2.93–3.00(2H, t), 4.27–4.34(2H, t).

Example 9

Synthesis of 3-(3-iodo-2-propynyloxy)-4-cyano-5-difluoromethylthioisothiazole (compound No. 12)

2.4 Grams of 3-(2-propynyloxy)-4-cyano-5-methylsulfonylisothiazole was dissolved in 50 ml of dioxane, a solution of 2 g of potassium hydrosulfide in 5 ml of water was added thereto, and then the reaction solution was stirred for 10 minutes. Thereafter, 20 g of 30% KOH was added, and chlorodifluoromethane was blown into the reaction solution for 30 minutes at room temperature with stirring. Water was added to the reaction solution, which was then extracted with ethyl acetate. The extract was washed with water, dried and concentrated under reduced pressure to obtain 2.2 g of the crude crystal of 3-(2-propynyloxy)-4-cyano-5-difluoromethylthioisothiazole. This product was dissolved in 20 ml of DMF, 4.5 g of iodine and 3.0 g of potassium iodide were added thereto with stirring, and then 7 g of 10% KOH was added dropwise with ice-cooling. After addition, the temperature of the reaction solution was returned to room temperature, and the reaction solution was stirred for 1 hour. Water was added to the reaction solution, which was then extracted with ethyl acetate. The extract was washed with water, dried and concentrated under reduced pressure to obtain crude crystals. The crude crystals were recrystallized from ether to obtain 2.9 g of crystals having a melting point of 106° to 107° C. (yield 80%).

NMR (CDCl$_3$) δ: 5.20(2H, s), 6.73–7.80(1H, t).

Example 10

Synthesis of 3-(3-iodo-1,1-dimethyl-2-propynyloxymethyloxy)-4-cyano-5-methylthioisothiazole (compound No. 100)

1.7 Grams of 3-hydroxy-4-cyano-5-methylthioisothiazole was dissolved in 30 ml of DMF, 1.4 g of 1,1-dimethyl-2-propynyloxymethyl chloride was added thereto, and then the reaction solution was stirred at 50° C. for 1 hour. Thereafter, the reaction solution was ice-cooled to 5° to 10° C., 5.1 g of iodine and 3.5 g of potassium iodide were added thereto, and then 6.6 g of 10% KOH was added dropwise. The temperature of the reaction solution was returned to room temperature, and after stirring for 1 hour, the reaction solution was extracted with ethyl acetate. The extract was washed with water, dried and concentrated under reduced pressure to obtain crude crystals. The crystals were recrystallized from ether to obtain 2.4 g of crystals having a melting point of 96° to 97° C. (yield 60%).

NMR (CDCl$_3$) δ: 1.55(6H, s), 2.66(3H, s), 5.78(2H, s).

Compounds of the formula (I) synthesized according to Examples will be shown in Table 1.

TABLE 1

| No. | R$^1$Y | R$^2$Z | Physical property m.p. (°C.) |
|---|---|---|---|
| 1 | I—C≡C—CH$_2$—O— | CH$_3$S— | 145–146 |
| 2 | I—C≡C—CH$_2$—O— | C$_2$H$_5$S— | 117–118 |
| 3 | I—C≡C—CH$_2$—O— | n-C$_3$H$_7$S— | 101.5 |
| 4 | I—C≡C—CH$_2$—O— | i-C$_3$H$_7$S— | 108–109 |
| 5 | I—C≡C—CH$_2$—O— | n-C$_4$H$_9$S— | 72–73 |
| 6 | I—C≡C—CH$_2$—O— | s-C$_4$H$_9$S— | 89–90 |
| 7 | I—C≡C—CH$_2$—O— | c-C$_5$H$_9$S— | 91–92 |
| 8 | I—C≡C—CH$_2$—O— | CH$_2$=CHCH$_2$—S— | 110–111 |
| 9 | I—C≡C—CH$_2$—O— | Cl—CH=CHCH$_2$—S— | 121–122 |
| 10 | I—C≡C—CH$_2$—O— | CH≡C—CH$_2$—S— | 115–116 |
| 11 | I—C≡C—CH$_2$—O— | CH≡C—CH$_2$CH$_2$—S— | 98–99 |
| 12 | I—C≡C—CH$_2$—O— | F$_2$CHS— | 106–107 |
| 13 | I—C≡C—CH$_2$—O— | F$_3$CCH$_2$S— | 88–89 |
| 14 | I—C≡C—CH$_2$—O— | F$_3$CCF$_2$CH$_2$S— | 75–76 |
| 15 | I—C≡C—CH$_2$—O— | CH$_3$OC$_2$H$_4$S— | 132–133 |
| 16 | I—C≡C—CH$_2$—O— | C$_2$H$_5$OC$_2$H$_4$S— | 121–123 |
| 17 | I—C≡C—CH$_2$—O— | NC—CH$_2$—S— | 165–167 |
| 18 | I—C≡C—CH$_2$—O— | CH$_3$C(O)—S— | 122–123 |
| 19 | I—C≡C—CH$_2$—O— | CH$_3$O$_2$C—CH$_2$—S— | 154–156 |
| 20 | I—C≡C—CH$_2$—O— | CH$_3$OC(O)—S— | 113–115 |
| 21 | I—C≡C—CH$_2$—O— | CH$_3$O— | 159–160 |
| 22 | I—C≡C—CH$_2$—O— | C$_2$H$_5$O— | 137–138 |
| 23 | I—C≡C—CH$_2$—O— | i-C$_3$H$_7$O— | 130–131 |
| 24 | I—C≡C—CH$_2$—O— | CH$_3$OC$_2$H$_4$O— | 112–113 |
| 25 | I—C≡C—CH$_2$—O— | NC—CH$_2$—O— | 167–168 |
| 26 | I—C≡C—CH$_2$—O— | CH$_2$=C(CH$_3$)CH$_2$—O— | 123–124 |
| 27 | I—C≡C—CH$_2$—O— | CF$_3$CH$_2$O— | 116–117 |
| 28 | I—C≡C—CH$_2$—O— | CH≡C—CH$_2$—O— | 111–113 |
| 29 | I—C≡C—CH$_2$—O— | i-C$_4$H$_9$O— | 120–121 |
| 30 | I—C≡C—CH$_2$—O— | (CH$_3$)$_2$N— | 171–172 |
| 31 | I—C≡C—CH$_2$—O— | (CH$_2$=CHCH$_2$)$_2$N— | 145–146 |
| 32 | I—C≡C—CH$_2$—O— | n-C$_4$H$_9$—N(CH$_3$)— | 124–125 |
| 33 | I—C≡C—CH$_2$—O— | C$_6$H$_5$CH$_2$—N(CH$_3$)— | 106–107 |
| 34 | I—C≡C—CH$_2$—O— | Q$_1$ | 152–153 |
| 35 | I—C≡C—CH$_2$—O— | Q$_2$ | 122–123 |
| 36 | I—C≡C—CH$_2$—O— | Q$_3$ | 146 (dec.) |
| 37 | I—C≡C—CH$_2$—O— | Q$_4$ | 155–156 |
| 38 | I—C≡C—CH$_2$—O— | CH$_2$=CHCH$_2$NH— | 127–129 |
| 39 | I—C≡C—CH$_2$—O— | i-C$_3$H$_7$NH— | 122–124 |
| 40 | I—C≡C—CH$_2$—O— | CH$_3$SO— | 149–151 |
| 41 | I—C≡C—CH$_2$—O— | CH$_3$SO$_2$— | 191–192 |
| 42 | I—C≡C—CH$_2$—O— | C$_2$H$_5$SO$_2$— | 157–158 |
| 43 | I—C≡C—CH$_2$—O— | F$_2$CHSO$_2$— | 145–147 |
| 44 | I—C≡C—CH$_2$—O— | F$_3$CCH$_2$SO$_2$— | 133–134 |
| 45 | I—C≡C—CH$_2$—O— | i-C$_3$H$_7$SO$_2$— | 141–142 |
| 46 | I—C≡C—CH$_2$—O— | c-C$_5$H$_9$SO$_2$— | 132–133 |
| 47 | I—C≡C—CH$_2$—O— | CH$_2$=CHCH$_2$—SO— | 102–104 |
| 48 | CH$_3$O— | I—C≡C—CH$_2$—O— | 92–93 |
| 49 | C$_2$H$_5$O— | I—C≡C—CH$_2$—O— | 88–89 |
| 50 | F$_2$CHO— | I—C≡C—CH$_2$—O— | 69–71 |
| 51 | i-C$_3$H$_7$O— | I—C≡C—CH$_2$—O— | 71–72 |
| 52 | HO— | I—C≡C—CH$_2$—O—CH$_2$—S— | 139.5 |
| 53 | CH$_3$O— | I—C≡C—CH$_2$—O—CH$_2$—S— | 124–125 |
| 54 | C$_2$H$_5$O— | I—C≡C—CH$_2$—O—CH$_2$—S— | 92–93 |
| 55 | n-C$_3$H$_7$O— | I—C≡C—CH$_2$—O—CH$_2$—S— | 77–78 |
| 56 | i-C$_3$H$_7$O— | I—C≡C—CH$_2$—O—CH$_2$—S— | 83–84 |
| 57 | CH$_2$=CHCH$_2$—O— | I—C≡C—CH$_2$—O—CH$_2$—S— | 67–68 |

TABLE 1-continued

| No. | R¹Y | R²Z | Physical property m.p. (°C.) |
|---|---|---|---|
| 58 | CH≡C—CH₂—O— | I—C≡C—CH₂—O—CH₂—S— | 58~59 |
| 59 | s-C₄H₉O— | I—C≡C—CH₂—O—CH₂—S— | 61~62 |
| 60 | F₂CHO— | I—C≡C—CH₂—O—CH₂—S— | 65~67 |
| 61 | F₃CCH₂O— | I—C≡C—CH₂—O—CH₂—S— | 56~57 |
| 62 | C₂H₅OC₂H₄O— | I—C≡C—CH₂—O—CH₂—S— | 73~74 |
| 63 | NC—CH₂O— | I—C≡C—CH₂—O—CH₂—S— | 105~107 |
| 64 | CH₃O₂C—CH₂—O— | I—C≡C—CH₂—O—CH₂—S— | 59~60 |
| 65 | C₂H₅O₂C—CH(CH₃)—O— | I—C≡C—CH₂—O—CH₂—S— | 82~84 |
| 66 | Cl—CH=CHCH₂—O— | I—C≡C—CH₂—O—CH₂—S— | 55~56 |
| 67 | CH₃C(O)—O— | I—C≡C—CH₂—O—CH₂—S— | 85~86 |
| 68 | CH₃O(O)C—O— | I—C≡C—CH₂—O—CH₂—S— | 76~77 |
| 69 | C₂H₅(O)C—O— | I—C≡C—CH₂—O—CH₂—S— | 65~66 |
| 70 | I—C≡C—CH₂CH₂—O— | CH₃S— | 102~103 |
| 71 | I—C≡C—CH₂CH₂—O— | C₂H₅S— | 88~89 |
| 72 | I—C≡C—CH₂CH₂—O— | i-C₃H₇S— | 81~82 |
| 73 | I—C≡C—CH₂CH₂—O— | CH₂=CHCH₂—S— | 76~78 |
| 74 | I—C≡C—CH₂CH₂—O— | C₂H₅OC₂H₄—S— | 84~85 |
| 75 | I—C≡C—CH₂CH₂—O— | CH₃O₂C—CH₂—S— | 114~115 |
| 76 | I—C≡C—CH₂CH₂—O— | F₂CHS— | 79~80 |
| 77 | I—C≡C—CH₂CH₂—O— | F₃CCH₂S— | 65~66 |
| 78 | I—C≡C—CH₂CH₂—O— | C₂H₅SO₂— | 137~138 |
| 79 | I—C≡C—CH₂CH₂—O— | F₂CHSO₂— | 125~126 |
| 80 | CH₃O— | I—C≡C—CH₂CH₂—O— | 71~73 |
| 81 | CH₃CH₂O— | I—C≡C—CH₂CH₂—O— | 65~66 |
| 82 | F₂CHO— | I—C≡C—CH₂CH₂—O— | 67~68 |
| 83 | i-C₃H₇O— | I—C≡C—CH₂CH₂—O— | 61~62 |
| 84 | CH₃OCH₂CH₂O— | I—C≡C—CH₂CH₂—O— | 71~72 |
| 85 | I—C≡C—CH₂—O—CH₂—O— | CH₃S— | 84~85 |
| 86 | I—C≡C—CH₂—O—CH₂—O— | C₂H₅S— | 57~58 |
| 87 | I—C≡C—CH₂—O—CH₂—O— | n-C₃H₇S— | 48~49 |
| 88 | I—C≡C—CH₂—O—CH₂—O— | i-C₃H₇S— | 51.5 |
| 89 | I—C≡C—CH₂—O—CH₂—O— | s-C₄H₉S— | 47~49 |
| 90 | I—C≡C—CH₂—O—CH₂—O— | F₂CHS— | 77~78 |
| 91 | I—C≡C—CH₂—O—CH₂—O— | F₃CCH₂S— | 66~67 |
| 92 | I—C≡C—CH₂—O—CH₂—O— | C₂H₅OCH₂CH₂S— | 69~70 |
| 93 | I—C≡C—CH₂—O—CH₂—O— | F₂CHSO₂— | 129~130 |
| 94 | I—C≡C—CH₂—O—CH₂—O— | C₂H₅SO₂— | 114~115 |
| 95 | I—C≡C—CH₂—O—CH₂—O— | CH₃O— | 76~77 |
| 96 | I—C≡C—CH₂—O—CH₂—O— | C₂H₅O— | 61~62 |
| 97 | I—C≡C—CH₂—O—CH₂—O— | CH₂=CHCH₂—O— | 55~57 |
| 98 | I—C≡C—CH₂—O—CH₂—O— | i-C₃H₇O— | 56~57 |
| 99 | I—C≡C—CH₂—O—CH₂—O— | F₃CCH₂O— | 49~50 |
| 100 | I—C≡C—C(CH₃)₂O—CH₂—O— | CH₃S— | 96~97 |
| 101 | I—C≡C—C(CH₃)₂O—CH₂—O— | C₂H₅S— | 71~72 |
| 102 | I—C≡C—C(CH₃)₂O—CH₂—O— | i-C₃H₇S— | 68~69 |
| 103 | I—C≡C—C(CH₃)₂O—CH₂—O— | CH₃SO₂— | 122~123 |
| 104 | I—C≡C—C(CH₃)₂O—CH₂—O— | F₂CHS— | 67~68 |
| 105 | I—C≡C—C(CH₃)₂—O—CH₂O— | CH₃O— | 88~89 |
| 106 | CH₃O— | I—C≡C—C(CH₃)₂O—CH₂—S— | 93~94 |
| 107 | F₂CHO— | I—C≡C—C(CH₃)₂O—CH₂—S— | 61~62 |
| 108 | C₂H₅O— | I—C≡C—C(CH₃)₂O—CH₂—S— | 57~58 |
| 109 | i-C₃H₇O— | I—C≡C—C(CH₃)₂O—CH₂—S— | 60~61 |
| 110 | I—C≡C—CH(CH₃)—O—CH₂—O— | CH₃S— | 89~90 |
| 111 | I—C≡C—CH(CH₃)—O—CH₂—O— | F₂CHS— | 76 |
| 112 | I—C≡C—CH(CH₃)—O—CH₂—O— | C₂H₅S— | 56~57 |
| 113 | I—C≡C—CH(CH₃)—O—CH₂—O— | C₂H₅SO₂— | 115.5 |
| 114 | I—C≡C—CH(CH₃)—O—CH₂—O— | C₂H₅O— | 52~53 |
| 115 | I—C≡C—CH(CH₃)—O—CH₂—O— | (CH₃)₂N— | 92~94 |
| 116 | I—C≡C—CH(CH₃)—O—CH₂—O— | CH₂=CHCH—NH— | 77~78 |
| 117 | I—C≡C—CH(CH₃)—O—CH₂—O— | i-C₃H₇NH— | 84~85 |
| 118 | I—C≡C—CH(CH₃)—O—CH₂—O— | Q₃ | 131 (dec.) |
| 119 | I—C≡C—CH₂—O—CH(CH₃)—O— | CH₃S— | 81~82 |
| 120 | I—C≡C—CH₂—O—CH(CH₃)—O— | CH₃SO₂— | 122~123 |
| 121 | I—C≡C—CH₂—O—CH(CH₃)—O— | CH₃O— | 75~76 |
| 122 | I—C≡C—CH₂—O—CH(CH₃)—O— | F₂CHS— | 70~71 |
| 123 | I—C≡C—CH₂—O—CH(CH₃)—O— | (CH₃)₂N— | 105~106 |
| 124 | I—C≡C—CH₂—O—CH(CH₃)—O— | i-C₃H₇—NH— | 84~85 |
| 125 | CH₃O— | I—C≡C—CH₂—O—CH(CH₃)—S— | 101~102 |
| 126 | C₂H₅O— | I—C≡C—CH₂—O—CH(CH₃)—S— | 96~97 |
| 127 | F₂CHO— | I—C≡C—CH₂—O—CH(CH₃)—S— | 92~93 |
| 128 | I—C≡C—CH₂—O—CH₂—S— | CH₃S— | 87~88 |
| 129 | I—C≡C—CH₂—O—CH₂—S— | C₂H₅S— | 79~80 |
| 130 | I—C≡C—CH₂—O—CH₂—S— | i-C₃H₇S— | 64~65 |
| 131 | I—C≡C—CH₂—O—CH₂—S— | s-C₄H₉S— | 51~52 |
| 132 | I—C≡C—CH₂—O—CH₂—S— | CH₂=CHCH₂—S— | 45~46 |
| 133 | I—C≡C—CH₂—O—CH₂—S— | CH₃OCH₂CH₂—S— | 61~62 |

TABLE 1-continued

| No. | R¹Y | R²Z | Physical property m.p. (°C.) |
|---|---|---|---|
| 134 | I—C≡C—CH₂—O—CH₂—S— | NC—CH₂—S— | 91–92 |
| 135 | I—C≡C—CH₂—O—CH₂—S— | c-C₅H₉—S— | 56–57 |
| 136 | CH₃S— | I—C≡C—CH₂—O—CH₂—S— | 112–113 |
| 137 | C₂H₅S— | I—C≡C—CH₂—O—CH₂—S— | 93–94 |
| 138 | F₂CHS— | I—C≡C—CH₂—O—CH₂—S— | 86–87 |
| 139 | i-C₃H₇S— | I—C≡C—CH₂—O—CH₂—S— | 91–92 |
| 140 | I—C≡C—CH₂—O—CH₂—S— | I—C≡C—CH₂—O—CH₂—S— | 103–104 |
| 141 | I—C≡C—CH₂—O—CH₂—O— | I—C≡C—CH₂—O—CH₂—S— | 114–115 |
| 142 | I—C≡C—CH₂—O— | I—C≡C—CH₂—O—CH₂—S— | 125–126 |

Of the compounds listed above, the followings are preferred; that is to say, Compound Nos. 1, 2, 12, 17, 21, 22, 41, 42, 43, 48, 49, 50, 52, 53, 54, 60, 80, 81, 82, 85, 86, 90, 95, 96, 97, 106, 107, 108, 119, 128, 129, 136 and 137. The most preferred compounds are Compound Nos. 12 and 96.

In the table, the expression "dec." means that decomposition of the compound occurred at said temperature, the expression "c-" means an alicyclic hydrocarbon group, and $Q_1$, $Q_2$, $Q_3$ and $Q_4$ mean the following chemical formulae, respectively:

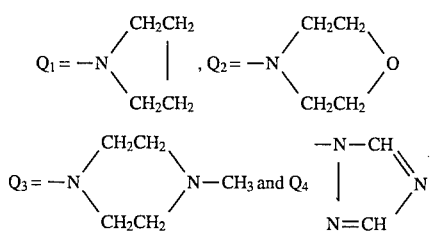

Prescription examples will be shown. In the examples, part is by weight.

| Formulation Example 1 | |
|---|---|
| Present compound | 50 parts |
| Xylene | 40 parts |
| Mixture of polyoxyethylene nonylphenyl ether and alkylbenzenesulfonic acid | 10 parts |

These materials are uniformly mixed into a solution to prepare an emulsifiable concentrate.

| Formulation Example 2 | |
|---|---|
| Present compound | 0.5 part |
| Xylene | 0.8 part |
| Kerosene | 98.7 parts |

These materials are uniformly mixed into a solution to prepare an oil spray.

| Formulation Example 3 | |
|---|---|
| Present compound | 3 parts |
| Clay powder | 82 parts |
| Diatomaceous earth powder | 15 parts |

These materials are uniformly mixed and pulverized to prepare a dust.

| Formulation Example 4 | |
|---|---|
| Present compound | 5 parts |
| Mixed powder of bentonite and clay | 90 parts |
| Calcium stearate | 1 part |

These materials are uniformly mixed, kneaded with a suitable amount of water, granulated and dried to prepare a granule.

| Formulation Example 5 | |
|---|---|
| Present compound | 20 parts |
| Mixture of kaolin and synthetic highly dispersible silicate | 75 parts |
| Mixture of polyoxyethylene nonylphenyl ether and calcium alkylbenzenesulfonate | 5 parts |

These materials are uniformly mixed and pulverized to prepare a wettable powder.

| Formulation Example 6 | |
|---|---|
| Present compound | 1 part |
| Polyethylene glycol 400 | 99 parts |

These materials are mixed into a solution to prepare a liquid formulation for coating.

| Formulation Example 7 | |
|---|---|
| Present compound | 2 parts |
| Polyethylene glycol 400 | 49 parts |
| Polyethylene glycol 4000 | 49 parts |

These materials are mixed into a solution with heating and then cooled to prepare an ointment.

| Formulation Example 8 | |
|---|---|
| Present compound | 3 parts |
| 1,2-Propanediol | 5 parts |
| Glycerol stearate | 5 parts |
| Spermaceti | 5 parts |
| Isopropyl myristate | 10 parts |
| Polysolvate | 4 parts |

These materials are mixed, heated and cooled, and 68 parts of water is added with heating to prepare a cream.

Test Example 1

Test for wood rotting-preventing effect

The following fungi were cultured in agar media, respectively, and mycelial disks on the media were stamped out together with the agar using a cork borer of 4 mm in diameter. The resulting mycelial disks on agar were used as an inoculum. Each test compound of 50 ppm was added to a malt extract agar medium and added in parts to Petri dishes. The above prepared inoculum was put on the Petri dishes and cultured at 28° C.±2° C. Two to ten days after inoculation, the diameter of the mycelial disk of each fungus was measured, and the mycelium growth-inhibitory rate was obtained according to the following equation.

Mycelium growth-inhibitory rate (%) =

$$\frac{\left(\begin{array}{c}\text{diameter of mycelium}\\ \text{in untreated plot}\end{array}\right) - \left(\begin{array}{c}\text{diameter of mycelium}\\ \text{in test plot}\end{array}\right)}{\text{diameter of mycelium in untreated plot}} \times 100$$

The mycelium growth-inhibitory rate (%) is indicated by the following symbols as a fungicidal effect on each fungus, and the results are shown in Table 2.

| Evaluation standard: Mycelium growth-inhibitory rate (%) | Rotting preventing effect |
|---|---|
| 100 ~ 95 | A |
| 94 ~ 80 | B |
| 79 ~ 60 | C |
| 59 ~ 0 | — |

Test fungi:
Basidomycetes
TYP: *Tyromyces palustris*
*Fungi Imperfecti*
TRV: *Trichoderma viride*
Ascomycetes
ASN: *Aspergillus niger*
Zygomycetes
RHN: *Rhizopus nigricans*

TABLE 2

| Compound No. | Rotting preventing effect | | | |
|---|---|---|---|---|
| | TYP | TRV | ASN | RHN |
| 1 | A | A | B | A |
| 2 | A | B | C | B |
| 7 | A | C | C | C |
| 10 | A | B | A | B |
| 12 | A | A | A | A |
| 16 | A | A | B | B |
| 20 | A | A | B | C |
| 21 | A | A | A | A |
| 22 | A | A | A | A |
| 23 | A | A | A | A |
| 30 | A | A | A | A |
| 35 | A | A | A | B |
| 36 | A | A | B | B |
| 41 | A | A | A | A |
| 43 | A | A | A | A |
| 46 | A | C | B | C |
| 48 | A | A | A | A |
| 51 | A | A | A | A |
| 53 | A | A | A | B |
| 54 | A | A | A | A |

TABLE 2-continued

| Compound No. | Rotting preventing effect | | | |
|---|---|---|---|---|
| | TYP | TRV | ASN | RHN |
| 57 | A | A | A | A |
| 60 | A | A | A | A |
| 67 | A | B | B | A |
| 70 | A | A | A | B |
| 72 | A | A | A | A |
| 78 | A | A | A | A |
| 80 | A | A | A | A |
| 82 | A | A | A | A |
| 84 | A | A | A | A |
| 85 | A | A | A | A |
| 86 | A | A | A | A |
| 87 | A | A | A | A |
| 90 | A | A | A | A |
| 94 | A | A | A | A |
| 95 | A | A | A | A |
| 96 | A | A | A | A |
| 98 | A | A | A | A |
| 100 | A | A | B | B |
| 103 | A | A | A | B |
| 106 | A | A | A | B |
| 110 | A | A | A | A |
| 111 | A | A | A | A |
| 115 | A | A | A | A |
| 119 | A | A | A | B |
| 122 | A | A | A | A |
| 126 | A | A | A | A |
| 127 | A | A | A | A |
| 129 | A | A | B | B |
| 132 | A | A | A | A |
| 136 | A | A | A | A |
| 138 | A | A | A | A |
| 142 | A | A | A | A |

Test Example 2

Test for phytopathogen controlling effect 2-1 Test for rice seed-disinfecting effect Unhulled rice infected with *Gibberella fujikuroi* ("Bakanae" disease of rice) was immersed in a test compound adjusted to 1000 ppm at 25° C. for 24 hours. Water was lightly swished off the seed, which was then sowed and germinated for two days. Three weeks after treatment with the solution containing the compound, the rate of the infected seedlings was examined, and the control of disease was calculated by comparison with that of the untreated plot. The control of disease was shown as a controlling effect on the basis of the following standard. The controlling effect of the present compound is shown in Table 3.

| Control of disease | Controlling effect |
|---|---|
| 100 ~ 95 | A |
| 94 ~ 80 | B |
| 79 ~ 60 | C |
| 59 ~ 0 | — |

2-2 Test for controlling effect on downy mildew of cucumber (*Pseudoperonospora cubensis*)

A test compound adjusted to 200 ppm was sprayed onto cucumber at the 2-leaf stage cultivated in pots. After one day, the cucumber was inoculated by spraying the zoospore suspension of *Pseudoperonospora cubensis*. After inoculation, the cucumber was placed in a 25° C.-humid room for 1 day and then in a greenhouse for 6 days. Thus, the cucumber was made to be infected with downy mildew. The control of disease of the test compound is calculated by comparing the degree of infection of each leaf with that in the untreated plot. The control of disease is shown as a controlling effect in the same manner as in Test Example 2-1. The results are shown in Table 3.

2-3 Test for controlling effect on sheath blight of rice (*Rhizoctonia solani*)

Rice seedlings at the 4-leaf stage were inoculated with the mycelium of sheath blight of rice (*Rhizoctonia solani*). After 24 hours, a test medicine solution adjusted to 200 ppm was sprayed onto the seedlings. After air-drying, the seedlings were placed in a humid room for 24 hours where the temperature was kept at 28° C. and humidity was kept at 98%. Thereafter, the seedlings were transferred to a greenhouse, and five days after inoculation, the degree of infected area was examined. The control of disease was calculated by comparison with that in the untreated plot. The control of disease is shown as a controlling effect in the same manner as in Test Example 2-1. The results are shown in Table 3.

TABLE 3

| Compound No. | Controlling effect | | |
|---|---|---|---|
| | "Bakanae" disease of rice | Downy mildew of cucumber | Sheath blight of rice |
| 1 | A | A | C |
| 4 | A | A | B |
| 8 | A | A | C |
| 12 | A | A | B |
| 15 | A | B | B |
| 17 | A | A | A |
| 20 | B | A | C |
| 21 | A | A | A |
| 23 | A | A | B |
| 30 | A | A | A |
| 32 | B | A | C |
| 35 | B | A | B |
| 41 | A | A | B |
| 43 | A | A | A |
| 47 | A | B | A |
| 48 | A | A | A |
| 50 | A | A | A |
| 53 | A | A | A |
| 54 | A | A | A |
| 60 | A | A | A |
| 63 | A | A | B |
| 67 | B | B | A |
| 70 | B | B | A |
| 78 | A | B | A |
| 80 | A | A | B |
| 82 | A | A | A |
| 86 | A | A | B |
| 90 | A | A | A |
| 94 | A | A | A |
| 96 | A | A | A |
| 100 | A | A | A |
| 103 | A | A | A |
| 106 | B | A | C |
| 110 | A | A | A |
| 114 | A | A | B |
| 115 | A | B | A |
| 119 | A | A | B |
| 122 | A | A | A |
| 125 | A | A | A |
| 127 | A | A | A |
| 128 | B | A | C |
| 136 | B | A | B |
| 140 | B | A | B |

Test Example 3

Test for an effect as antimycotic agent 3-1 In vitro antimycotic activity on Candida albicans Candida albicans IFO 1270 pre-cultured on a Sabouraud's glucose agar (SGA) plate medium at 37° C. for hours was suspended in a sterilized physiological salt solution. The number of fungi in the resulting suspension was counted with a globulimeter, and adjusted so as to be $1\times10^7$ cell/ml with a sterilized physiological salt solution. This solution was used as an inoculum solution. Thereafter, 0.1 ml of this solution and 0.1 ml of a dimethyl sulfoxide (DMSO) solution of the test compound were added to 9.8 ml of Sabouraud's glucose broth (SGB), and shake-cultured at 37° C. for 48 hours. After culture, the medium turbidity was measured at 650 nm, and the growth-inhibitory rate of the fungus was calculated according to the following equation.

Growth inhibitory rate (%)=(1−W/Y)×100

Y: Medium turbidity of DMSO control group

W: Medium turbidity of test compound group

From this inhibitory rate, the antimycotic activity was shown by the symbols A to D. The test results of the test compounds are shown in Table 4.

| A: Growth inhibitory rate | 100% |
|---|---|
| B: Growth inhibitory rate | 99 ~ 85% |
| C: Growth inhibitory rate | 84 ~ 60% |
| D: Growth inhibitory rate | 59 ~ 0% |

3-2 In vitro antimycotic activity on *Aspergillus fumigatus*.

To *Aspergillus fumigatus* TIMM 0063 precultured at 37° C. for 48 hours on a potato dextrose agar (PDA) slant medium was added a sterilized physiological salt solution containing 0.1%(W/V) Tween 80. After conidia were made free from the solution, the solution was filtered through a sterilized two-sheet gauze to remove the mycelium mass. The number of the conidia in the resulting suspension was counted with a globulimeter and adjusted so as to be $1\times10^5$ conidia/ml with a sterilized physiological salt solution containing 0.1%(W/V) Tween 80. This solution was used as an inoculum solution. Casitone agar plate medium containing the DMSO solution of the test compound in a rate of 1% (V/V) was inoculated with the inoculum solution at four places thereof with a microplanter, and cultured with the medium allowed to stand at 37° C. for 48 hours. After culture, the diameter of the mycelium disks cultivated at the four inoculated parts was measured, and its mean value was obtained. The growth inhibitory rate was calculated according to the following equation, and the antimycotic activity was shown in the same manner as in Test Example 3-1. The test results of the test compounds are shown in Table 4.

Growth inhibitory rate (%)=(1−W'/Y')×100

Y': Diameter of mycelium disk of DMSO control group

W': Diameter of mycelium disk of test compound group 3-3 In vitro antimicrobial activity on *Trichophyton mentagrophytes* To *Trichophyton mentagrophytes* IFO 5810 precultured at 27° C. for 2 to 3 weeks on a Sabouraud's glucose agar (SGA) slant medium was added a sterilized physiological salt solution containing 0.1% (W/V) Tween 80. After conidia were made free from the solution, the solution was filtered through a sterilized two-sheet gauze to remove the mycelium mass. The number of the conidia in the resulting suspension was counted with a globulimeter and adjusted so as to be $1\times10^6$ conidia/ml with a sterilized physiological salt solution containing 0.1%(W/V) Tween 80. This solution was used as an inoculum solution. Thereafter, 0.1 ml of this solution and 0.1 ml of the dimethyl sulfoxide (DMSO)

solution of the test compound were added to 9.8 ml of Sabouraud's glucose broth (SGB), and shake-cultured at 27° C. for 7 days. After culture, the degree of growth of the fungus was observed with the naked eye, and the antimicrobial activity was shown according to the following judgement standard.

A: Fungus is not observed at all with the naked eye.

B: Presence of fungus is slightly observed on shaking the test tube.

C: Fungus of about less than one-fourth that of the DMSO control group is observed with the naked eye.

D: Fungus of about less than half that of the DMSO control group is observed with the naked eye.

The same degree of number of the fungi as that of the DMSO control group is observed with the naked eye.

TABLE 4

| | Antimycotic activity | | |
|---|---|---|---|
| Compound No. | C.albicans 10 (ppm) | A.fumigatus 10 (ppm) | T.mentagrophytes 10 (ppm) |
| 1 | A | A | A |
| 4 | A | A | A |
| 12 | A | A | A |
| 16 | A | A | A |
| 21 | A | A | A |
| 22 | A | A | A |
| 23 | A | A | A |
| 29 | A | A | A |
| 30 | A | A | A |
| 36 | A | A | A |
| 41 | A | A | A |
| 43 | A | A | A |
| 48 | A | A | A |
| 50 | A | A | A |
| 54 | A | A | A |
| 56 | A | A | A |
| 57 | A | A | A |
| 60 | A | A | A |
| 63 | A | A | A |
| 70 | A | A | A |
| 71 | A | A | A |
| 82 | A | A | A |
| 83 | A | A | A |
| 88 | A | A | A |
| 90 | A | A | A |
| 96 | A | A | A |
| 101 | A | A | A |
| 106 | A | A | A |
| 107 | A | A | A |
| 111 | A | A | A |
| 119 | A | A | A |
| 123 | A | A | A |
| 125 | A | A | A |
| 128 | A | A | A |
| 136 | A | A | A |
| 138 | A | A | A |
| 141 | A | A | A |

What is claimed is:

1. An isothiazole derivative represented by the formula (I),

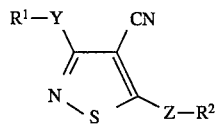

wherein $R^1$ represents a hydrogen atom, $C_1$–$C_6$ alkyl, $C_2$–$C_7$ alkenyl, $C_3$–$C_7$ alkynyl, $C_3$–$C_7$ cycloalkyl, $C_1$–$C_6$ cyanoalkyl, $C_1$–$C_6$ haloalkyl, $C_2$–$C_7$ alkoxyalkyl, $C_3$–$C_7$ alkoxycarbonylalkyl, $C_2$–$C_7$ haloalkenyl, $C_2$–$C_7$ alkylcarbonyl, $C_2$–$C_7$ alkoxycarbonyl, iodoalkynyl or iodoalkynyloxyalkyl group, $R^2$ represents a $C_1$–$C_6$ alkyl, $C_2$–$C_7$ alkenyl, $C_3$–$C_7$ alkynyl, $C_3$–$C_7$ cycloalkyl, $C_1$–$C_6$ cyanoalkyl, $C_1$–$C_6$ haloalkyl, $C_2$–$C_7$ alkoxyalkyl, $C_3$–$C_7$ alkoxycarbonylalkyl, $C_2$–$C_7$ haloalkenyl, $C_2$–$C_7$ alkylcarbonyl, $C_2$–$C_7$ alkoxycarbonyl, iodoalkynyl or iodoalkynyloxyalkyl group, provided that at least one of $R^1$ and $R^2$ represents an iodoalkynyl or iodoalkynyloxyalkyl group, Y represents O or S, and Z represents O, S, SO, $SO_2$ or $NR^3$ in which $R^3$ represents a hydrogen atom, $C_1$–$C_6$ alkyl, $C_2$–$C_7$ alkenyl, $C_3$–$C_7$ alkynyl or benzyl group, or $R^3$ and $R^2$, taken together, represent a $C_3$–$C_5$ alkylene group which may contain O or N.

2. An isothiazole derivative according to claim 1, wherein $R^1$ is an iodoalkynyl or iodoalkynyloxyalkyl group, $R^2$ is $C_1$–$C_4$ alkyl, $C_2$–$C_5$ alkenyl, $C_1$–$C_4$ haloalkyl or $C_1$–$C_4$ cyanoalkyl group, Y is O or S, and Z is O, S or $SO_2$.

3. An isothiazole derivative according to claim 1, wherein $R^1$ is $C_1$–$C_4$ alkyl, $C_2$–$C_5$ alkenyl or $C_1$–$C_4$ haloalkyl group, $R^2$ is an iodoalkynyl or iodoalkynyloxyalkyl, Y is O or S, and Z is O, S or $SO_2$.

4. An isothiazole derivative according to claim 1, wherein $R^1$ is iodopropargyl or iodopropargyloxymethyl group, $R^2$ is $C_1$–$C_2$ alkyl, allyl, difluoromethyl or cyanomethyl group, Y is O, and Z is O or S.

5. An isothiazole derivative according to claim 1, wherein $R^1$ is $C_1$–$C_2$ alkyl, allyl or difluoromethyl group, $R^2$ is iodopropargyl or iodopropargyloxymethyl group, Y is O, and Z is O or S.

6. A fungicidal or bactericidal composition containing as an active ingredient an isothiazole derivative represented by the formula (I),

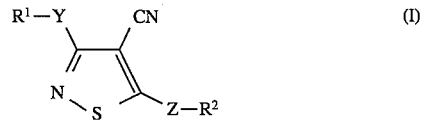

wherein $R^1$ represents a hydrogen atom, $C_1$–$C_6$ alkyl, $C_2$–$C_7$ alkenyl, $C_3$–$C_7$ alkynyl, $C_3$–$C_7$ cycloalkyl, $C_1$–$C_6$ cyanoalkyl, $C_1$–$C_6$ haloalkyl, $C_2$–$C_7$ alkoxyalkyl, $C_3$–$C_7$ alkoxycarbonylalkyl, $C_2$–$C_7$ haloalkenyl, $C_2$–$C_7$ alkylcarbonyl, $C_2$–$C_7$ alkoxycarbonyl, iodoalkynyl or iodoalkynyloxyalkyl group, $R^2$ represents a $C_1$–$C_6$ alkyl, $C_2$–$C_7$ alkenyl, $C_3$–$C_7$ alkynyl, $C_3$–$C_7$ cycloalkyl, $C_1$–$C_6$ cyanoalkyl, $C_1$–$C_6$ haloalkyl, $C_2$–$C_7$ alkoxyalkyl, $C_3$–$C_7$ alkoxycarbonylalkyl, $C_2$–$C_7$ haloalkenyl, $C_2$–$C_7$ alkylcarbonyl, $C_2$–$C_7$ alkoxycarbonyl, iodoalkynyl or iodoalkynyloxyalkyl group, provided that at least one of $R^1$ and $R^2$ represents an iodoalkynyl or iodoalkynyloxyalkyl group, Y represents O or S, and Z represents O, S, SO, $SO_2$ or $NR^3$ in which $R^3$ represents a hydrogen atom, $C_1$–$C_6$ alkyl, $C_2$–$C_7$ alkenyl, $C_3$–$C_7$ alkynyl or benzyl group, or $R^3$ and $R^2$, taken together, represent a $C_3$–$C_5$ alkylene group which may contain O or N, and an inert carrier.

7. A composition according to claim 6 for the protection of industrial materials from decay.

8. A composition according to claim 6 for use in agriculture and horticulture.

9. A composition according to claim 6 for use in medical treatment.

* * * * *

UNITED STATES PATENT AND TRADEMARK OFFICE
CERTIFICATE OF CORRECTION

PATENT NO. : 5,578,622
DATED : November 26, 1996
INVENTOR(S) : Ikeda, et. al.

It is certified that error appears in the above-identified patent and that said Letters Patent is hereby corrected as shown below:

Title page, item [73], Assignee: should read--  NIHON NOHYAKU CO., LTD., Tokyo, Japan --

Signed and Sealed this

Tenth Day of February, 1998

Attest:

BRUCE LEHMAN

*Attesting Officer*  *Commissioner of Patents and Trademarks*